(12) United States Patent
Grebius

(10) Patent No.: US 7,513,679 B2
(45) Date of Patent: Apr. 7, 2009

(54) DEVICE FOR MIXING AND DELIVERING BONE CEMENT

(75) Inventor: Staffan Grebius, Lund (SE)

(73) Assignee: Asept Medical AB, Lund (SE)

( * ) Notice: Subject to any disclaimer, the term of this patent is extended or adjusted under 35 U.S.C. 154(b) by 606 days.

(21) Appl. No.: 10/518,962

(22) PCT Filed: Jun. 23, 2003

(86) PCT No.: PCT/SE03/01070

§ 371 (c)(1),
(2), (4) Date: Jun. 27, 2005

(87) PCT Pub. No.: WO2004/002615

PCT Pub. Date: Jan. 8, 2004

(65) Prior Publication Data

US 2005/0254340 A1    Nov. 17, 2005

(30) Foreign Application Priority Data

Jun. 28, 2002    (SE) ................................. 0202018

(51) Int. Cl.
*B01F 15/02* (2006.01)
*G01F 11/00* (2006.01)
(52) U.S. Cl. ...................................... 366/189
(58) Field of Classification Search ............... 366/139, 366/189; 222/243, 260, 282, 308, 386; 606/92, 606/93, 94
See application file for complete search history.

(56) References Cited

U.S. PATENT DOCUMENTS

| 1,612,996 | A | * | 1/1927 | Waagbo | 222/252 |
|---|---|---|---|---|---|
| 1,694,845 | A | * | 12/1928 | De Trey | 366/333 |
| 1,998,692 | A | * | 4/1935 | Harrison et al. | 366/333 |
| 2,825,134 | A | * | 3/1958 | Hicks | 433/90 |
| 3,140,078 | A | * | 7/1964 | Grubb et al. | 366/256 |
| 3,475,010 | A | * | 10/1969 | Moline et al. | 366/333 |
| 4,277,184 | A | * | 7/1981 | Solomon | 366/139 |
| 4,340,056 | A | * | 7/1982 | Erb | 604/82 |
| 4,371,094 | A | * | 2/1983 | Hutter, III | 222/1 |
| 4,676,655 | A | * | 6/1987 | Handler | 366/130 |
| 4,799,801 | A | * | 1/1989 | Bruning | 366/255 |
| 4,966,468 | A | * | 10/1990 | Bruning | 366/333 |
| 5,000,738 | A | * | 3/1991 | LaVallo et al. | 604/110 |

(Continued)

FOREIGN PATENT DOCUMENTS

EP    0 603871 B1    6/1994

(Continued)

*Primary Examiner*—Tony G Soohoo
(74) *Attorney, Agent, or Firm*—Merchant & Gould P.C.

(57) ABSTRACT

Device for mixing and applying a paste such as bone cement or the like, including a cylinder 3 receiving the paste, a piston 1 reciprocable in the cylinder 3, a piston rod 2 displaceable and rotatable in the piston 1 and forming mixing means 21 for paste received in the cylinder 3, and latch means for interconnecting the piston 1 and the piston rod 2 to allow displacement of the piston 1 in the cylinder 3 by means of the piston rod 2 for deposition of the paste outside the cylinder 2, characterized in that means are provided for locking the piston rod 2 to the piston 1 by jamming, said means allowing the piston rod 2 to be locked to the piston 1 at any position along the complete length of the piston rod 2.

9 Claims, 7 Drawing Sheets

U.S. PATENT DOCUMENTS

| | | |
|---|---|---|
| 5,398,483 A | 3/1995 | Smith et al. |
| 5,842,786 A * | 12/1998 | Solomon .................... 366/139 |
| 5,951,160 A | 9/1999 | Ronk |
| 6,367,962 B1 * | 4/2002 | Mizutani et al. ............ 366/189 |
| 6,406,175 B1 * | 6/2002 | Marino ....................... 366/130 |
| 6,431,743 B1 * | 8/2002 | Mizutani et al. ............ 366/189 |
| 6,547,432 B2 * | 4/2003 | Coffeen et al. .............. 366/130 |
| 6,550,957 B2 * | 4/2003 | Mizutani et al. ............ 366/189 |
| 6,736,537 B2 * | 5/2004 | Coffeen et al. .............. 366/130 |
| 6,755,563 B2 * | 6/2004 | Wahlig et al. ............... 366/139 |
| 2005/0105384 A1 * | 5/2005 | Eder et al. ................... 366/139 |
| 2005/0128867 A1 * | 6/2005 | Henniges et al. ............ 366/139 |

FOREIGN PATENT DOCUMENTS

WO          01/83094 A1          9/2001

* cited by examiner

DEVICE FOR MIXING AND DELIVERING BONE CEMENT

SUMMARY OF THE INVENTION

This invention relates to a device for mixing and delivering pastes that require mixing prior to delivering, and more particularly to a single use device that is able to handle high viscosity pastes, like e.g. bone cement.

The device is of the type including means for mixing and applying a paste such as bone cement or the like, including a cylinder receiving the paste, a piston reciprocable in the cylinder, a piston rod displaceable and rotatable in the piston and forming mixing means for paste received in the cylinder, and latch means for interconnecting the piston and the piston rod to allow displacement of the piston in the cylinder by means of the piston rod for deposition of the paste outside the cylinder

BACKGROUND OF THE INVENTION

Bone cement is used e.g. in connection with surgical replacement of a hip joint. Bone cement generally consists of akrylate plastic, which is biocompatible. Depending on the use, bone cement has got different viscosity characteristics. For use in connection with hip joint replacements, the viscosity is often quite high, whereas the bone cement used for e.g. spinal disc enhancements has lower viscosity. This invention mainly relates to mixing and application of bone cements with higher viscosity, but is just as useful for low viscosity applications.

For simplicity, the term bone cement will be used throughout this application, although the invention can be used for any other kind of paste that requires mixing prior to application.

Presently, mixing of bone cement ingredients is mostly done in a separate vessel, whereupon the mixed bone cement is put into a bone cement applicator that generally is made of stainless steel. This method has some severe drawbacks:

1. Mixing of the bone cement should preferably be performed under vacuum, since low ambient pressure reduces the presence of gas impurities in the bone cement, that leads to a connection with reduced strength. The vacuum treatment is often performed after the components of the bone cement have been mixed. Applying the prior art method, the mixed (and vacuum treated) bone cement must be put into an applicator, which increases the risk of adding gas impurities to the bone cement.
2. The applicator is usually not of single use type, which makes it necessary to disassemble the applicator to be able to clean it and sterilize it properly after it has been used. Additionally, the applicator wears down by time.

The object of this invention is to provide a single use mixer/applicator in which the bone cement is mixed under vacuum and that is capable of handling bone cement with high viscosity.

BACKGROUND ART

U.S. Pat. No. 5,951,160 discloses a bone cement applicator that uses the piston rod as the bone cement mixing means. After the mixing has been performed, the piston rod is withdrawn towards the piston, whereupon two wings on the distal end of the piston rod are passed through a slot in the piston to be introduced into a cavity therein. Then, the rod is rotated slightly and the piston rod becomes secured to the piston by the wings received in the cavity. This prior art device is simple, but has got some severe drawbacks:

1. It is not possible to use the device for high viscosity bone cement, since high viscosity bone cement will clog the slot in the piston and make it impossible to engage the wings on the piston rod with the piston.
2. The mixing cannot be performed under vacuum, since there are no withholding means for the piston that prevents the piston from being displaced in the cylinder by the force of the vacuum.
3. The mixing quality is poor, since there are only two wings on the end of the piston rod.

Additionally, the applicator according to U.S. Pat. No. 5,951,160 is not provided with means facilitating the extrusion of bone cement from the cylinder, which means that the device must be put into some kind of device to facilitate the extrusion of the bone cement.

U.S. Pat. No. 5,398,483 discloses a device and a method for application of bone cement, wherein the bone cement components are contained separated in a cartridge. When the bone cement is to be used, the sealing between the cartridge compartments is opened to allow the bone cement components to be mixed in the cartridge. After mixing the cartridge is placed in an applicator gun. This method has one large disadvantage: it is not possible to use any kind of additional components (like e.g. antibiotics), since the bone cement comes in a prepackaged, sealed cartridge.

Cem-Vac Inc. sell a combined device in which a piston for extruding the bone cement is located at one end of a cylinder and a piston for mixing the bone cement is located at the other end of the cylinder. The bone cement components are supplied to the cylinder through a hollow mixing piston rod. After the mixing is complete, the device is placed in a pistol grip applicator, and the hollow piston rod is used as an applicator nozzle.

The prior art devices mentioned above use a separate pistol grip applicator for applying the required pressure to the bone cement.

The present invention aims to overcome the abovementioned and other problems by providing a device in which the bone cement can be mixed under vacuum, which includes means for facilitating the application, and which can be discarded after use.

SUMMARY OF THE INVENTION

The present invention provides a device for mixing and delivering bone cement of the kind referred to above, which is characterised in that means are provided for locking the piston rod to the piston by jamming, said means allowing the piston rod to be locked to the piston at any position along the complete length of the piston rod.

Preferred details of the invention are defined in the dependent claims.

INDUSTRIAL APPLICABILITY

As the population in the world's industrialised parts grow older, the need for different surgical corrections of the shortcomings of the human body becomes more intense. For example, 15000 hip and knee joint replacements occur in Sweden only, every year. For most of these hip or knee joint replacements, bone cement is used for fastening the manmade hip or knee joint in the medullary canal of femur.

Since the speed at which the surgeon can work is important from a number of views, it is of importance to provide a device in which the bone cement can be mixed and from which the bone cement can be deposited. It is also of importance that the device can be discarded after use, so that no personnel resources must be used for cleaning and disinfecting the device after use.

DETAILED DESCRIPTION OF A PREFERRED EMBODIMENT

Figure 1:
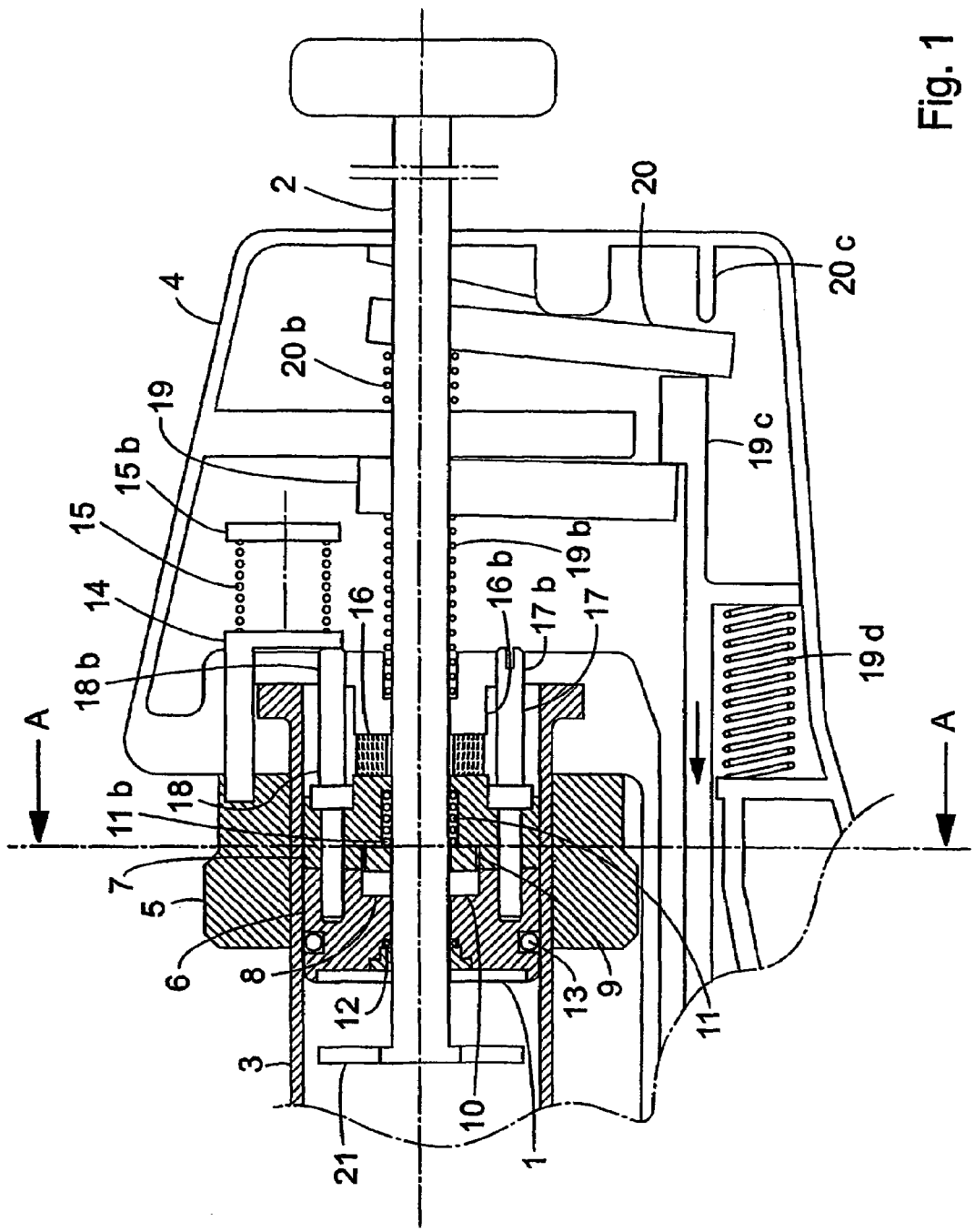
FIGS. 1 and 2 are fragmentary axial cross sectional views of the proximal end portion of the device showing the interaction between the piston and the piston rod.
Figure 4:
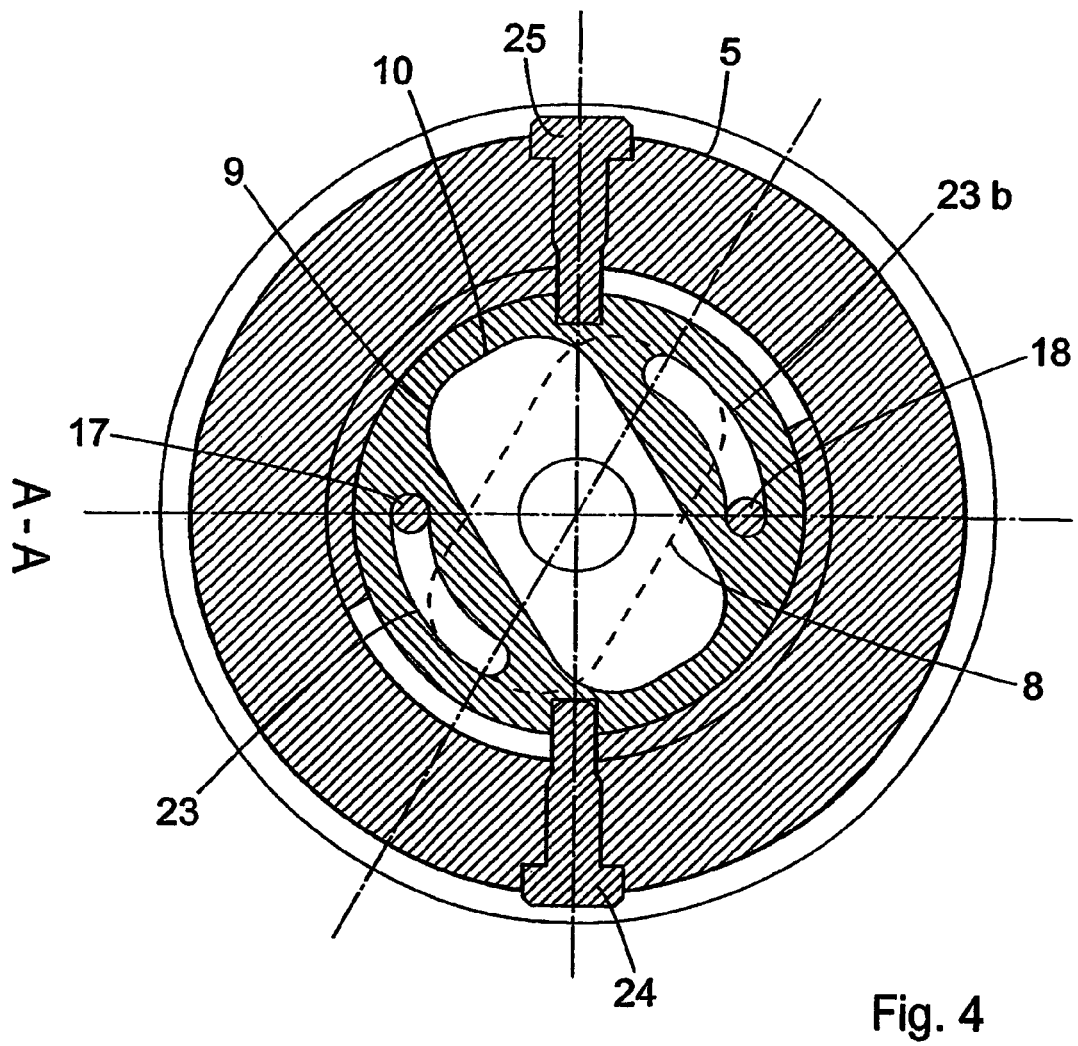
FIG. 4 is a cross sectional view taken along line A-A in FIG. 1.

FIG. 1 shows a piston 1, a piston rod 2, a proximal end portion of a cylinder 3 and a part of a main housing 4. On the outside of the cylinder 3 an external ring 5, rotatable on the cylinder, is provided. The piston is divided into a front component 6 and a back component 7, which engage each other at plane surfaces. In each of the piston components 6, 7 there is provided in plane surface, a recess 8,9, respectively, which recesses 8,9 are placed at an angle with respect to each other, as shown in FIG. 4. A lock member 10 with a central opening through which the piston rod 2 is displaceably received is located in recess 9 and is biased by a helical pressure spring 11, housed in a recess 11b in the back component 7 of the piston 1, to rest upon the surface of the front component 6 of the piston 1.

The front component 6 of the piston 1 is provided with sealing means 12,13, which seal the connections piston 1/cylinder 3 and piston 1/piston rod 2.

Ring securing means 14 are provided to prevent the ring 5 from being rotated. The ring securing means 14 is biased by a helical pressure spring 15, which rests upon an abutment 15b in the housing 4. Behind the piston 1, an elastic body 16 is provided, that rests between a tubular boss 16b formed by the housing, and the back component 7 of the piston 1. The piston rod 2 is slidable through all components of the piston 1.

Two pins 17,18 are provided to prevent the front component 6 of the piston 1 from rotating by being firmly attached to the front component 6 of the piston 1, and run in two holes 17b, 18b provided in the main housing 4. Except from serving as means preventing the front component 6 of the piston 1 from rotating, the pins 16, 17 also serve to hold the piston components 6,7 together. The back component 7 of the piston 1 is provided with two slots 23, 23b (see FIG. 4), formed to allow the back component 7 to rotate with respect to the front component 6.

On the front end of the piston rod 2 mixing means 21 are provided. The mixing means 21 act to mix the constituents of the paste housed in the cylinder 3 upon reciprocal movement and rotation of the piston rod 2, and may be in form of several radial wings extending from the distal end of the piston rod 2.

Figure 2:
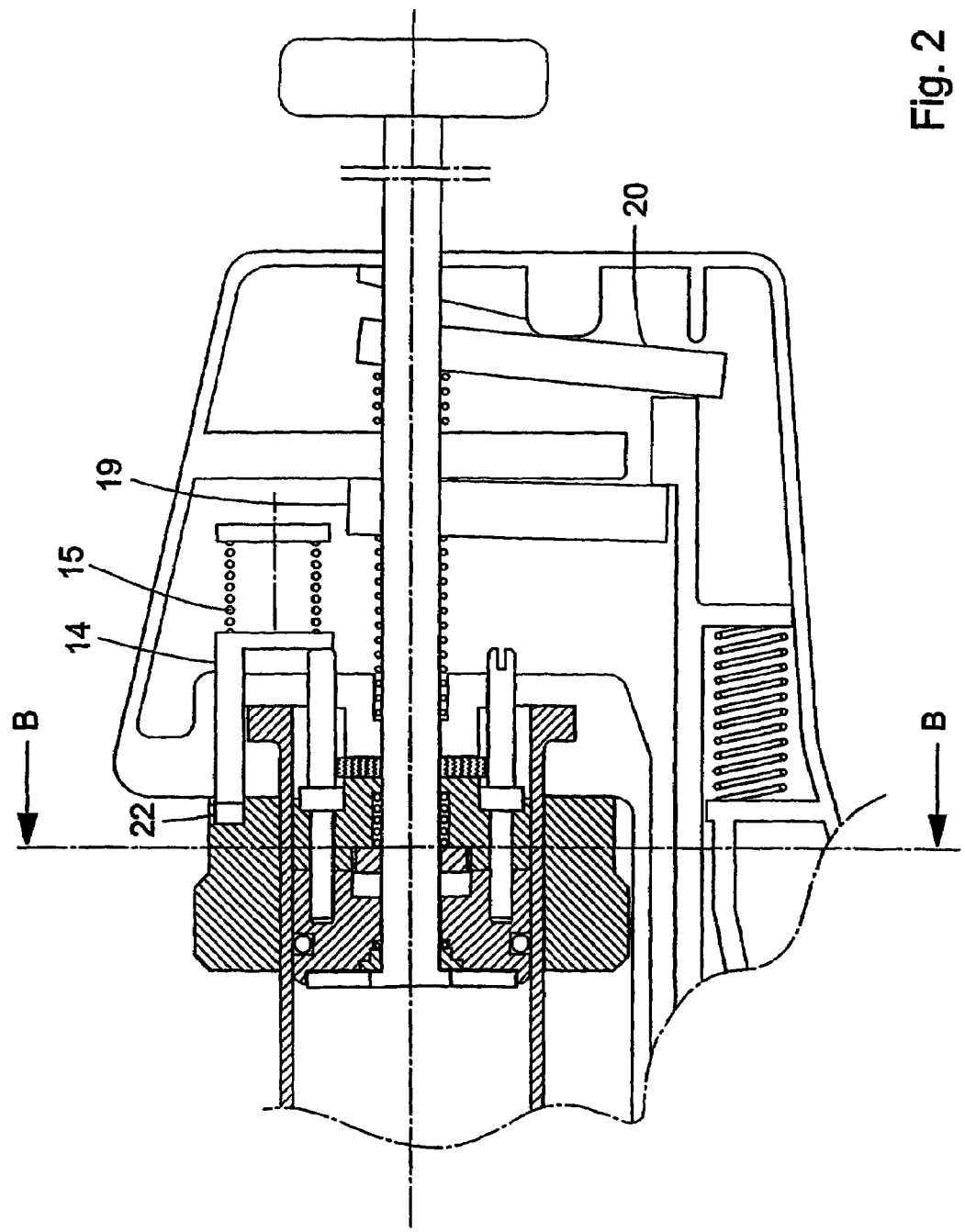

In FIG. 2, the piston 1 has been pulled backwards by force applied to the piston rod 2, compressing the elastic body 16, the ring securing means 14 being lifted from recesses 22 in the external ring 5, which makes it possible to rotate the external ring 5. Since the external ring 5 is connected to the back component 7 of the piston 1 by means of small pins 24,25 (shown in FIG. 5), the back component 7 will rotate as well, which is allowed by the design of slots 23 (shown in FIG. 4). As the back component 7 of the piston 1 is rotated by rotating the external ring 5, and the front component 6 is held against rotation by the pins 16, 17, the recesses 8,9 will overlap. This leads to the lock member 10 falling down into the recess 8 in the front component 6 of the piston 1. The lock member 10 falling down into the recess 8 irreversibly locks the piston 1 to the piston rod 2 in the forward direction. It is however possible to let the piston 1 slide along the piston rod 2 towards the proximal end of the device. As will be explained below, this is advantageous in some aspects.

Figure 3:
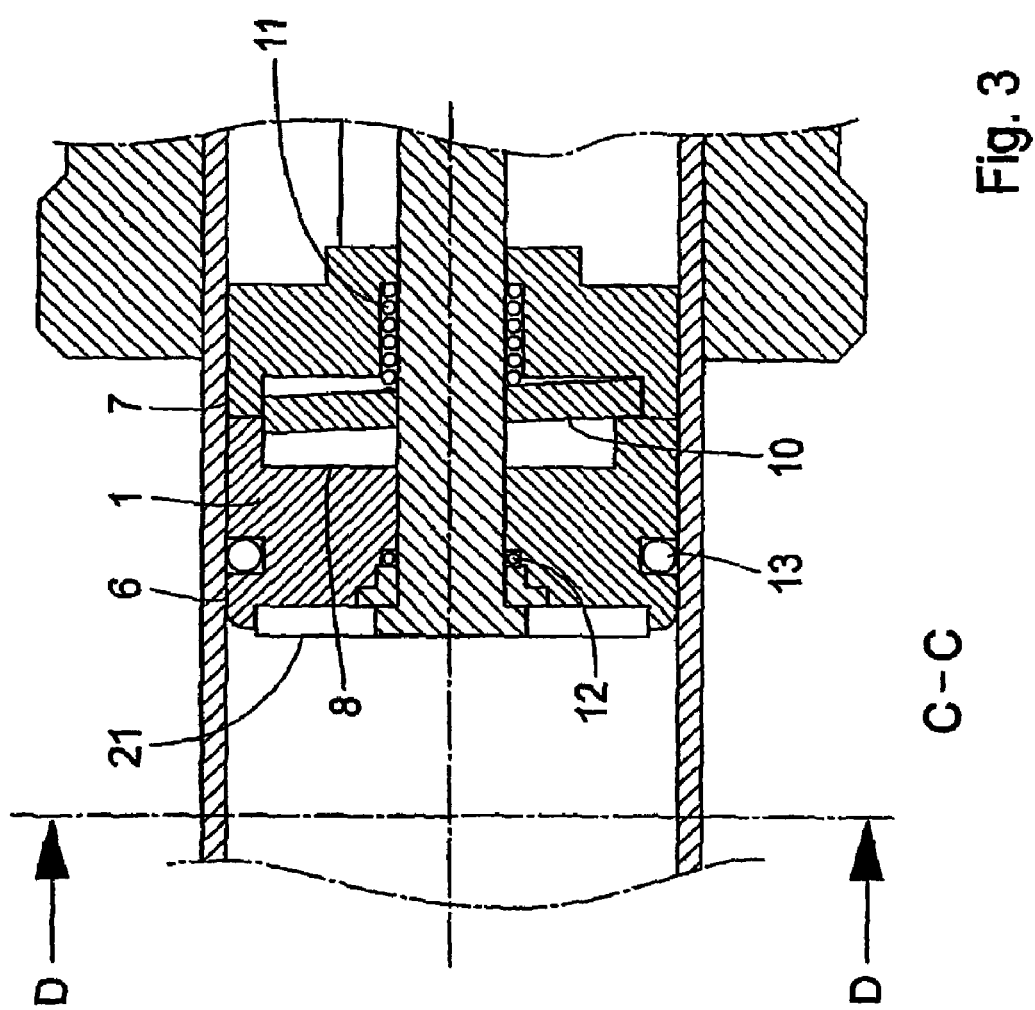
FIG. 3 is a fragmentary enlarged axial cross sectional view showing the interlocking between the piston and the piston rod.

The locking action between the lock member 10 and the piston rod 2 is shown in FIG. 3, which shows the lock member 10 interacting with the recess 8 in the front component 6 of the piston 1. Since the lock member 10 is supported on only one side, laterally displaced from the centre axis of the piston rod 2, the lock member 10 jams the piston rod 1 in the forward direction.

FIG. 4 shows the lock member 10 in its recess 9 in the back component 7 of the piston 1 before it has fallen down into the recess 8 in the front component 6 of the piston 1. Also shown is (dashed) the contour of the recess 8 in the front component 6 of the piston 1. Furthermore, the position of the two pins 17, 18 and their corresponding slots 23 in the back component 7 of the piston 1 are shown. The two small pins 24 and 25 connect the external ring 5 with the back component 7 of the piston 1.

As the piston 1 is locked to the piston rod 2, the extrusion of paste from the cylinder 3 can be started by starting to move the piston 1 forward by means of the piston rod 2. As the piston 1 moves forward, the connection between the piston 1 and the main housing 4 by the pins 16,17 releases, just as the connection between the external ring 5 and the back component 7 of the piston 1.

Figure 5:
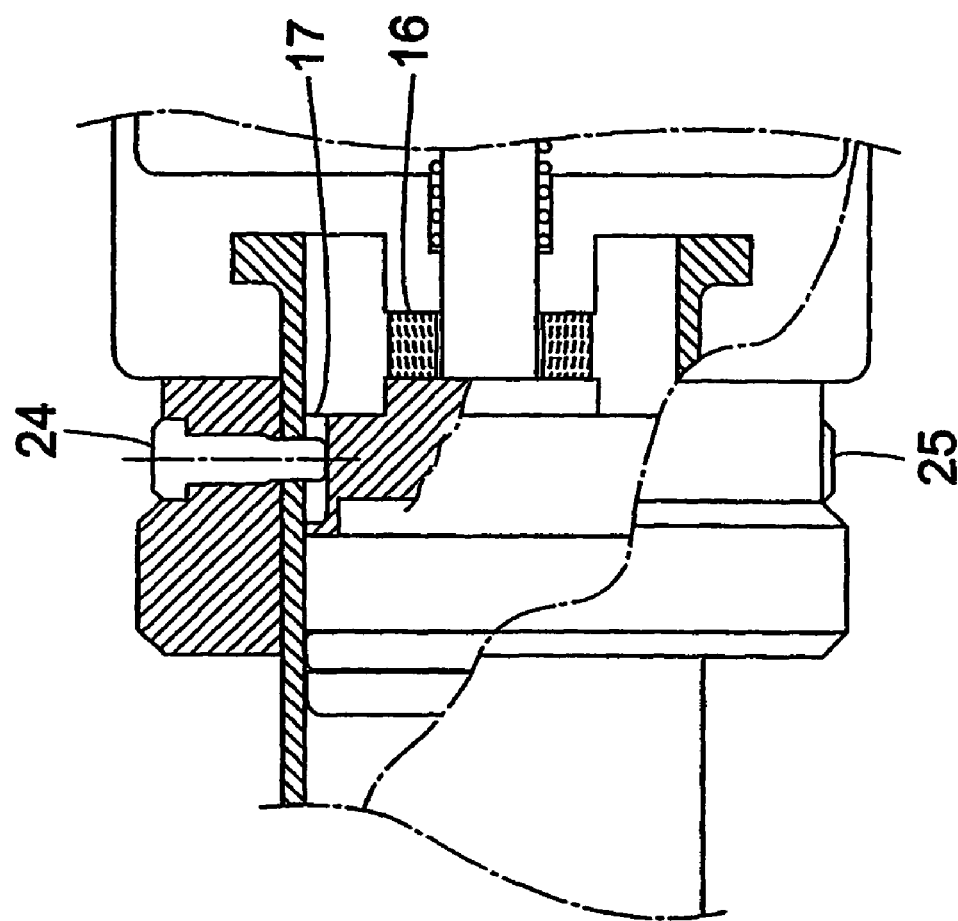
FIGS. 5 and 6 are fragmentary axial cross sectional views showing the interaction between the piston and an external ring.

FIG. 5 shows an example of how the interaction between the external ring 5 and the back component 7 of the piston 1 can be designed. The two small pins 24, 25 are received in two open slits, one of which is shown at 26, in the back component 7 of the piston 1. The two slits are open to allow forward motion of the piston 1.

Figure 6:
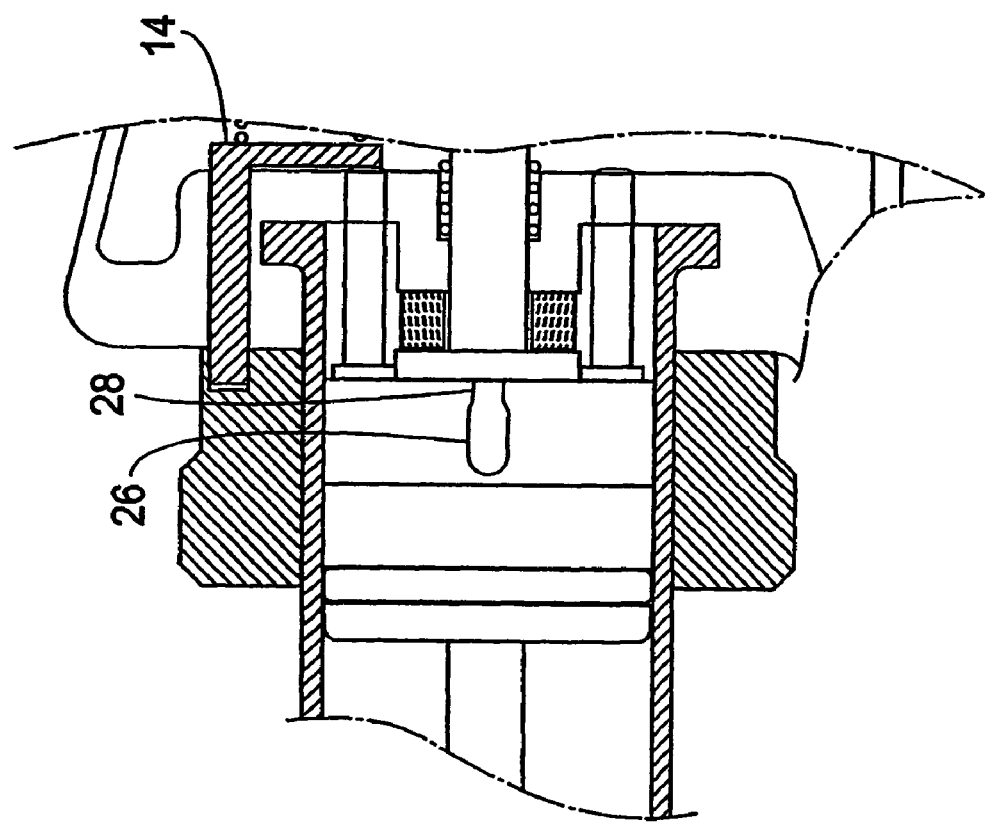

Two open slits, one of which is shown in FIG. 6 at 26, are provided each with a restriction, one of which is shown at 28. The restrictions serve to restrict forward motion of the piston 1 without applying a substantial force to the piston 1. They also serve to give a distinct click as the piston 1 commences its travel forward to extrude the paste housed in the cylinder 3, and thereby tells the user that the unit is ready for applying the paste.

All details mentioned above are housed in the main housing 4 including pressing means 19 and locking means 20 that act on the piston rod 2. The pressing means 19 are biased by a helical pressure spring 19b, one end of which acts on the tubular boss 16b, the other end on the pressing means 19. The helical pressure spring 19b serves to press the pressing means 19 towards the proximal end of the device. The locking means 20 are spring loaded by a helical pressure spring 20b, which presses the locking means 20 backwards. The locking means 20 can be deactivated by being pressed towards the projection 20c. Both the pressing means 19 and the locking means 20 are actuated by a bar 19c, that in turn is connected to some kind of power grip, e.g. a pistol grip.

The function of the pressing 19 and locking means 20 is as follows: When the power grip is actuated, the bar 19c will travel forward (in the direction of the arrow shown in FIG. 1), activating the locking means 20 by releasing said means from the projection 20c, biased by the helical pressure spring 20b. Simultaneously, the bar 19c acts on the pressing means 19, which leads to a jamming effect between the pressing means 19 and the piston rod 2, pressing the piston rod 2 forward under compression of the helical pressure spring 19b. During the forward moving procedure of the piston rod 2, the locking means slide along the piston rod 2.

As the power grip is released, the jamming effect between the pressing means 19 and the piston rod 2 discontinues, which leads to the helical pressure spring 19b pressing the pressing means 19 back along the piston rod 2. If the power grip is totally released, the bar 19c will remove the jamming action between the locking means 20 and the piston rod 2 by forcing (the force emanating from helical pressure spring 19d) the locking means 20 towards the projection 20c.

Figure 7:
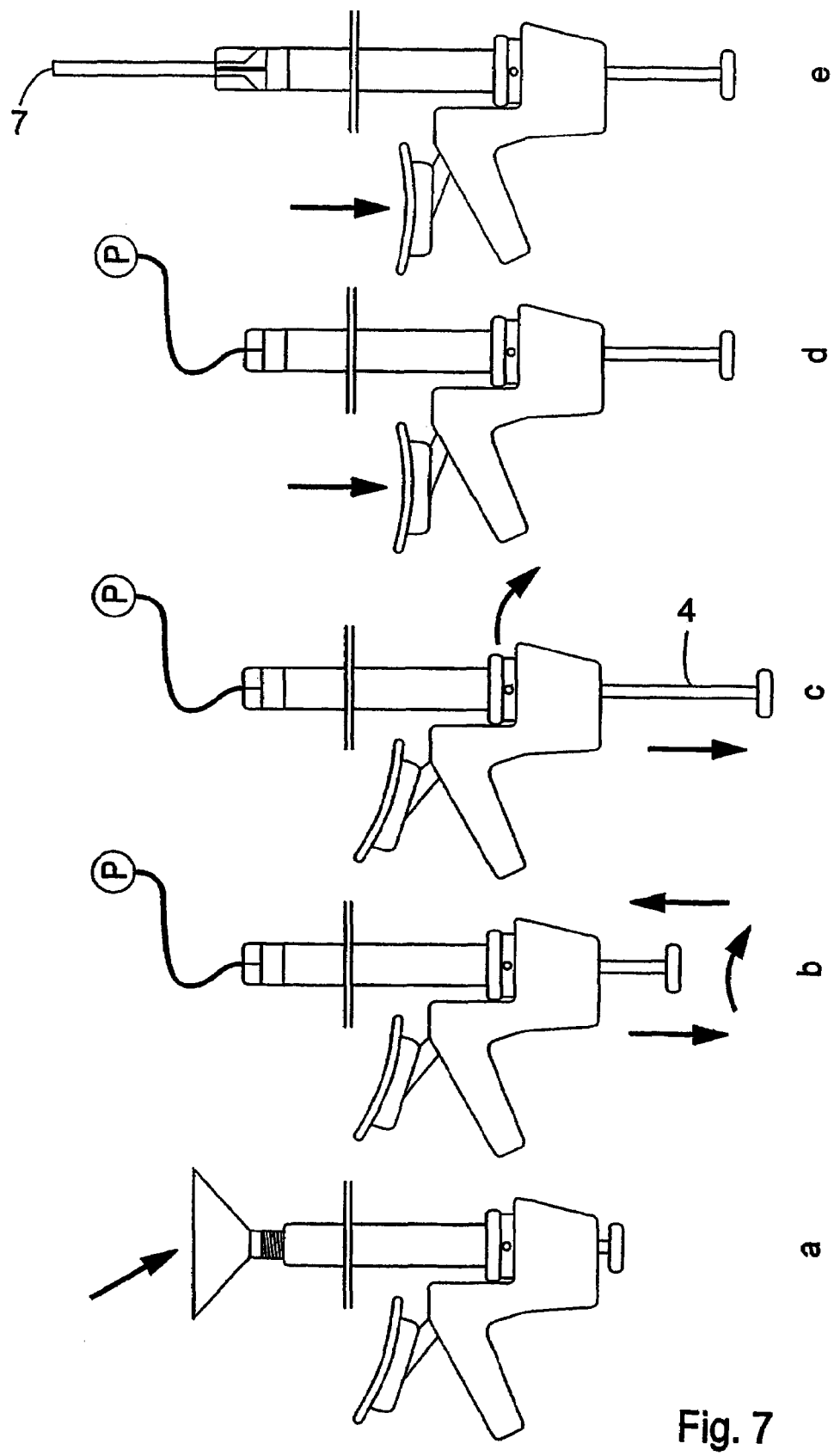
FIG. 7a-e show five different operation steps of the device.

In the position where the power grip is totally released, the piston rod 2 is not in any way restricted from being pushed and pulled back and forth (or being rotated) through the components in the main housing, allowing mixing of the paste constituents In the following, the function of the device will be described, with reference to the components mentioned above, and to FIG. 7.

In the first step, the components of the paste that is to be mixed and applied are introduced into the cylinder 3. After the paste components have been received in the cylinder 3, the cylinder 3 is connected to a vacuum source P, that reduces the presence of gases in the paste, both such gases that emanate from air being mixed into the paste and gases that are formed as a result from the curing process of the paste.

By pushing and pulling the piston rod 2 back and forth and rotating it, the mixing means 21 on the distal end of the piston rod 2 mixes the components of the paste. These operational steps are shown in FIGS. 7a and b.

The next sequential step is to lock the piston rod 2 to the piston 1. This is accomplished by pulling the piston rod 2 forcefully backwards and simultaneously turning the external ring 5, as shown in FIG. 7c.

In FIG. 7d, the power grip is actuated, leading to the piston being pushed forward, whereby the paste fills out any empty spaces in the cylinder 3, as the vacuum source P is still connected to the cylinder.

In FIG. 7d, the vacuum source P is disconnected from the cylinder 3 and a nozzle is attached to the front end of the cylinder 3. The nozzle can have different configurations depending on what kind of application the device should be used for.

If the piston rod 2 would slip forward without taking the piston 1 forward and hence not extrude any paste, the piston rod 2 can be retracted and the extrusion of paste can be recommenced.

One very important feature of the function of the device is that it is not necessary that the piston rod 2 is completely withdrawn towards the piston 1 to be able to lock the piston 1 to the piston rod 2, as is the case with the prior art device described in U.S. Pat. No. 5,951,160. If enough force is applied to the piston 1, it is possible to turn the external ring 5 and hence lock the piston 1 to the piston rod 2. This feature is very important, since it makes it possible to lock the piston 1 to the piston rod 2 even if high viscosity paste would make it too hard to pull the piston rod 2 so far that the mixing means 21 comes in physical contact with the piston 1.

One further advantage with the embodiment in which a lock member 10 is falling down into a recess 8 is that it irreversibly locks the piston 1 to the piston rod 2, which prevents the unit from being used more than once.

The invention claimed is:

1. A single use device for mixing and applying a paste such as bone cement, including a cylinder receiving the paste, a piston reciprocable in the cylinder, a piston rod displaceable and rotatable in the piston and forming mixing means for paste received in the cylinder, and latch means for interconnecting the piston and the piston rod to allow displacement of the piston in the cylinder by means of the piston rod for deposition of the paste outside the cylinder, wherein jamming means are provided for locking the piston rod to the piston, said jamming means allowing the piston rod to be locked to the piston at any position along the complete length of the piston rod.

2. The single use device according to claim 1, wherein the piston is divided into front and back components rotatable relative one another.

3. The single use device according to claim 1, wherein the cylinder is gas tight, which enables mixing of the paste under vacuum.

4. The single use device according to claim 1, wherein the jamming means in the piston include a lock member with a central hole receiving the piston rod, which member in the jamming position is supported in a position laterally displaced relative to the centre axis of the piston rod.

5. The single use device according to claim 1, wherein an external ring on the cylinder is rotatable for locking of the piston to the piston rod.

6. The single use device according to claim 5, wherein the external ring is secured by securing means, to prevent the ring from being turned accidentally.

7. The single use device according to claim 5, wherein the piston rod is restricted from being pulled backwards by an elastic body provided behind the piston.

8. The single use device according to claim 1, wherein the piston is provided with sealing means to ensure the gastightness of the cylinder.

9. The single use device according to claim 1, wherein single use is guaranteed by the jamming means which irreversibly locks the piston to the piston rod.

* * * * *

UNITED STATES PATENT AND TRADEMARK OFFICE
CERTIFICATE OF CORRECTION

PATENT NO. : 7,513,679 B2
APPLICATION NO. : 10/518962
DATED : April 7, 2009
INVENTOR(S) : Staffan Grebius It is certified that error appears in the above-identified patent and that said Letters Patent is hereby corrected as shown below:

Column 1, line 4 "SUMMARY OF THE INVENTION" should read -- FIELD OF THE INVENTION --

Signed and Sealed this

Twenty-fifth Day of August, 2009

David J. Kappos
*Director of the United States Patent and Trademark Office*